United States Patent
Holleman et al.

(10) Patent No.: US 7,242,987 B2
(45) Date of Patent: *Jul. 10, 2007

(54) MEDICAL LEAD ADAPTOR

(75) Inventors: Timothy W. Holleman, Ham Lake, MN (US); Andrew J. Ries, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 505 days.

This patent is subject to a terminal disclaimer.

(21) Appl. No.: 10/465,158

(22) Filed: Jun. 19, 2003

(65) Prior Publication Data

US 2004/0260355 A1    Dec. 23, 2004

(51) Int. Cl.
*A61N 1/05* (2006.01)
(52) U.S. Cl. ........................ 607/122; 607/119
(58) Field of Classification Search ............. 607/36, 607/37, 116, 119
See application file for complete search history.

(56) References Cited

U.S. PATENT DOCUMENTS

| | | | |
|---|---|---|---|
| 4,142,532 A | 3/1979 | Ware | |
| 4,182,345 A | 1/1980 | Grose | |
| 4,393,883 A * | 7/1983 | Smyth et al. | 607/123 |
| 4,628,934 A | 12/1986 | Pohndorf et al. | 128/419 PG |
| 5,070,605 A | 12/1991 | Daglow et al. | |
| 5,235,978 A | 8/1993 | Hirschberg et al. | 607/5 |
| 5,328,442 A * | 7/1994 | Levine | 600/17 |
| 5,366,496 A | 11/1994 | Dahl et al. | 607/132 |
| 5,470,346 A | 11/1995 | Adams | 607/37 |
| 5,683,445 A | 11/1997 | Swoyer | 607/125 |
| 5,766,042 A | 6/1998 | Ries et al. | |
| 5,797,970 A | 8/1998 | Pouvreau | 607/9 |
| 6,212,434 B1 * | 4/2001 | Scheiner et al. | 607/123 |
| 6,466,824 B1 | 10/2002 | Struble | 607/115 |
| 6,505,082 B1 * | 1/2003 | Scheiner et al. | 607/123 |
| 6,901,289 B2 * | 5/2005 | Dahl et al. | 607/9 |
| 2002/0103522 A1 * | 8/2002 | Swoyer et al. | 607/116 |
| 2003/0077943 A1 | 4/2003 | Osypka | |
| 2004/0064176 A1 * | 4/2004 | Min et al. | 607/126 |

FOREIGN PATENT DOCUMENTS

| | | |
|---|---|---|
| EP | 0 598 617 A2 | 5/1994 |
| EP | 0 599 567 | 6/1994 |
| WO | WO 03/035173 A1 | 5/2003 |

OTHER PUBLICATIONS

The Connector Task Force of the Pacemaker Committee, AAMI "Application Form for New Project," AAMI, p. 1-7,PAC No. 1-5 (Mar. 17, 2001).

* cited by examiner

*Primary Examiner*—Carl Layno
*Assistant Examiner*—Tammie K. Heller
(74) *Attorney, Agent, or Firm*—Carol F. Barry; Girma Wolde-Michael (57) ABSTRACT

An adaptor couples multiple high-voltage connector elements included on a plurality of medical electrical lead connectors to a single connector port of an implantable medical device thereby facilitating alternative high-voltage therapy vectors.

10 Claims, 6 Drawing Sheets

MEDICAL LEAD ADAPTOR

FIELD OF THE INVENTION

The present invention relates generally to adaptors for connecting medical electrical leads to implantable medical devices (IMDs) and, more particularly, to an adaptor for connecting more than one medical lead, each having a high-voltage connector terminal, to a single connector port of an IMD.

BACKGROUND OF THE INVENTION

In the field of therapeutic electrical stimulation, it is often desirable to provide electrical connection of more than one lead to a single connection port of a medical device. In particular, in the field of cardiac pacing, it is sometimes necessary to provide electrical connection of two leads to a single connection port of an IMD, e.g. a cardiac pacemaker or implantable cardioverter defibrillator, such that stimulation pulses may be delivered to more than one cardiac site or across a desired vector.

Medical lead connectors have been standardized in the industry. For example IS-1 pacing/sensing connectors are available in unipolar or bipolar configurations, including one or two electrical contacts, respectively, for making connection between a unipolar pace/sense electrode or a bipolar pace/sense electrode pair and an IMD; DF-1 connectors are available for making a high-voltage connection between an IMD and a defibrillation electrode via a single a single electrical contact. Other contemplated standards define connectors for making both high-voltage and low-voltage connections between an IMD and multiple electrodes; one such standard defines a connector including two high voltage contacts and two low voltage contacts, effectively combining two unipolar DF-1 connectors and a bipolar IS-1 connector into a single connector in order to provide electrical coupling to two high-voltage electrodes and a bipolar pace/sense electrode pair carried on a single, quadripolar lead for pacing and defibrillating the heart.

Clinical experience has shown that, in some patients, an acceptable defibrillation threshold cannot be reached using two high-voltage electrodes located on a single lead. In these patients, it becomes necessary to implant more than one lead in order to create an effective vector for the delivery of defibrillation energy. It is therefore desirable to provide a medical lead adaptor that allows connection of two connectors, each including a high voltage contact, to a single connector port of an IMD.

BRIEF DESCRIPTION OF THE DRAWINGS

Embodiments of the present invention will be more readily understood from the following detailed description when considered in conjunction with the drawings, in which like reference numerals indicate identical structures throughout the several views, and wherein.

The drawings are not necessarily to scale.

DETAILED DESCRIPTION OF THE INVENTION

Figure 1:
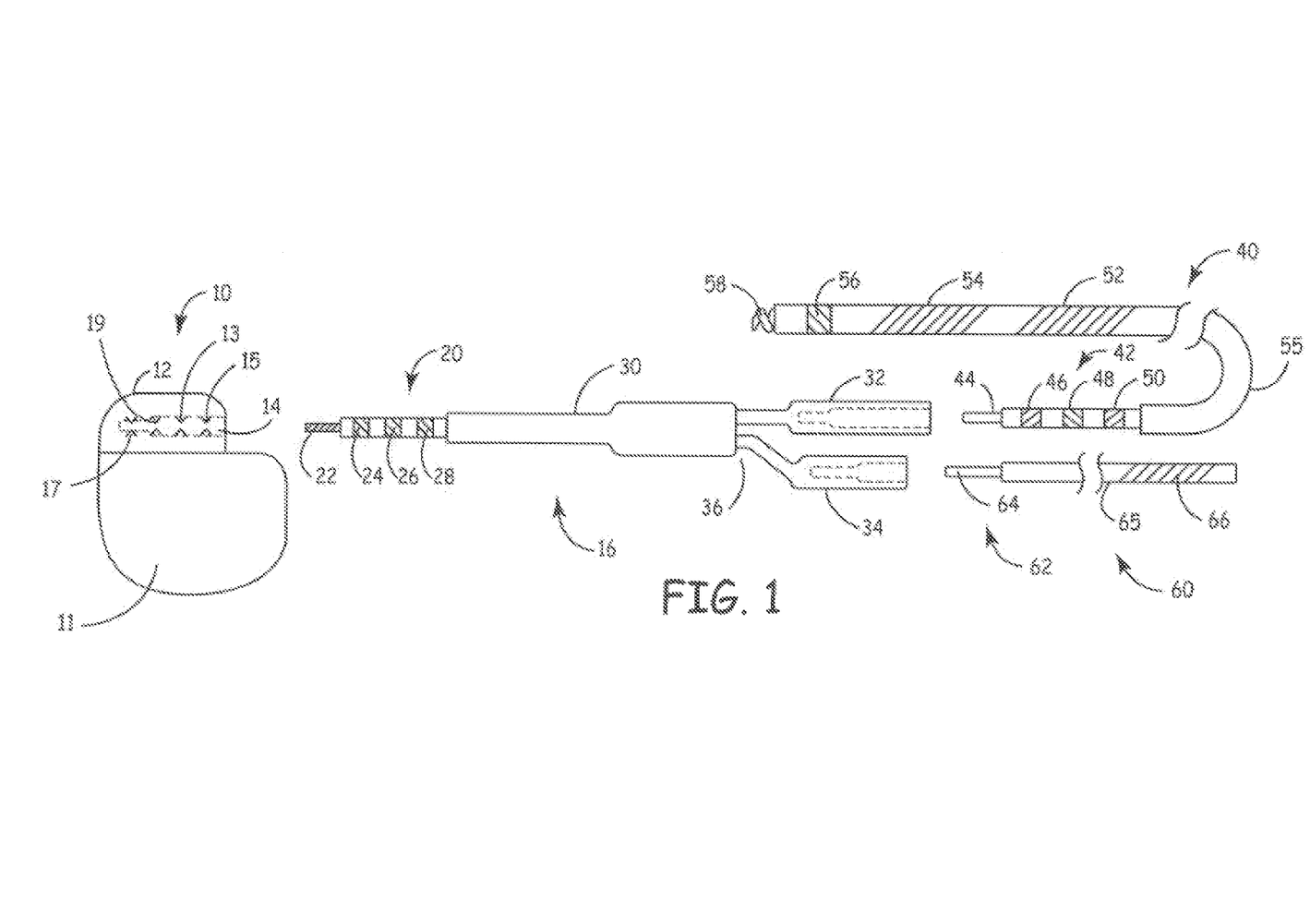
FIG. 1 is plan view of a medical system including a lead adaptor according to an embodiment of the present invention.

FIG. 1 is plan view of a medical system including a lead adaptor 16 according to an embodiment of the present invention. FIG. 1 illustrates the medical system including the adaptor 16 provided to couple a first lead 40 and a second lead 60 to an IMD 10. As illustrated in FIG. 1, first lead 40 includes a tip electrode 58 and ring electrode 56, which provide a low-voltage therapy, for example pacing and sensing, and two coil electrodes 52 and 54, which provide high-voltage therapy, for example defibrillation. Each electrode 52, 54, 56, and 58 is electrically connected to a corresponding connector element 50, 48, 46, and 44, respectively, located on a lead connector terminal 42 via electrically isolated conductors carried by a lead body 55. FIG. 1 further illustrates second lead 60 including a coil electrode 66 for high voltage therapy; electrode 66 is electrically connected to a connector pin 64 included in a lead connector terminal 62 via an insulated conductor carried by a lead body 65. According to embodiments of the present invention, if electrodes 54 and 52 of first lead 40, when implanted in a patient, cannot be positioned to provide an acceptable defibrillation threshold, electrode 66 of second lead 60 is implanted in a position where it may be employed to improve the threshold, and both first lead 40 and second lead 60 are coupled to a single connector port 14 of IMD 10 via adaptor 16.

Adaptor 16 includes a connector terminal 20 adapted to engage within connector port 14 of a connector header 12 of IMD 10, and, as illustrated in FIG. 1, connector terminal 20 includes three connector rings 24, 26 and 28 and a connector pin 22. Connector header 12 is shown attached to a hermetically sealed enclosure or can 11 that contains a battery and electronic circuitry and other components. Can 11 may further serve as a high voltage electrode in conjunction with lead electrodes 54, 52, 66. Port 14, configured to receive either first lead connector terminal 42 or adaptor connector terminal 20, includes high-voltage connectors 13 and 15 of any of the known types that are electrically connected to the electronic circuitry through feedthrough pins of feedthroughs (not shown) mounted to extend through can 11. Connectors 13 and 15 are dimensioned in diameter and are spaced apart in port 14 to receive and make electrical and mechanical connection with connector rings 26 and 28, respectively, of adaptor connector terminal 20, or with connector elements 48 and 50 of lead connector terminal 42. Such electrical and mechanical connection is effected either through the tightening of setscrews (not shown) as disclosed in U.S. Pat. Nos. 4,142,532 and 4,182,345, for example, or an action of inwardly extending force beams (not shown) as disclosed in U.S. Pat. Nos. 5,070,605 and 5,766,042, for example. Additional connectors 17 and 19 included in port 14 make mechanical and electrical contact with connector pin 22 and connector ring 24 of adaptor connector terminal 20 or with connector elements 44 and 46 of lead connector terminal 42. According to one embodiment of the present invention, connector pin 22 and connector ring 24 are adapted for low-voltage coupling in port 14 while connector rings 26 and 28 are adapted for high-voltage coupling in port 14. According to alternate embodiments of the present invention any two of connector rings 24, 26, 28 and connector pin 22 may be eliminated and a remaining two be adapted for high-voltage coupling in port 14.

As illustrated in FIG. 1, adaptor 16 further includes a first receptacle port 32 and a second receptacle port 34 extending from a bifurcation 36 of an insulating body 30, which carries and electrically isolates conductors (not shown) extending from connector pin 22 and connector rings 24, 26, and 28 of adaptor connector terminal 20 to corresponding contacts included in receptacle ports 32 and 34. First port 32 and second port 34 are adapted to engage first lead connector 42 and second lead connector 62, respectively, providing electrical coupling for at least the high voltage electrodes of each lead. In some embodiments, second lead connector 62 conforms to the DF-1 connector standard.

Figure 2:
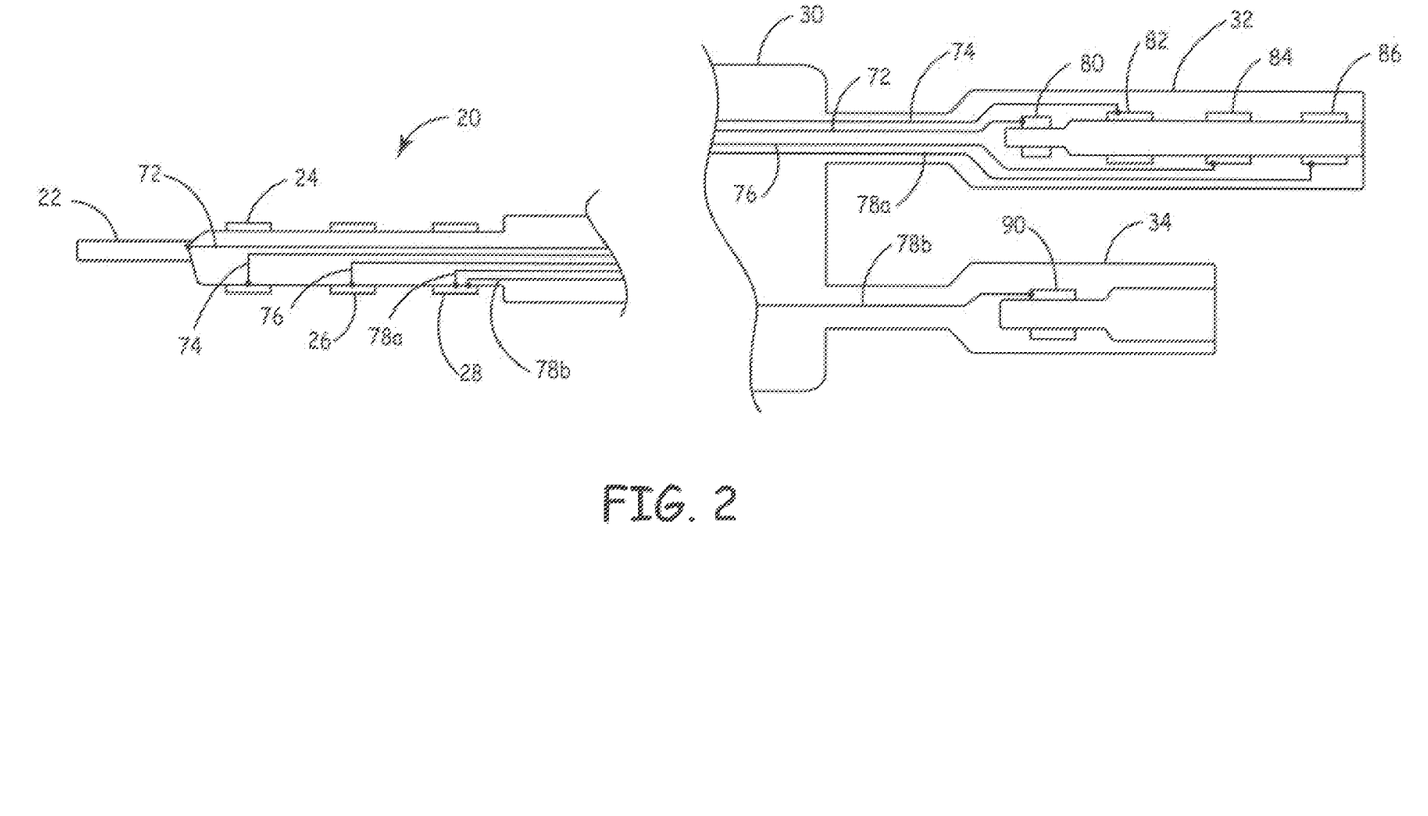
FIG. 2 is a sectional view of the adaptor of FIG. 1.

FIG. 2 is a sectional view of adaptor 16 wherein receptacle port 32 is shown to include low-voltage contacts 80 and 82 and high-voltage contacts 84 and 86 for providing electrical connection to lead connector elements 44, 46, 48, and 50 respectively (FIG. 1); contact 80 is coupled to connector pin 22 and via a conductor 72 and each of contacts 82, 84, and 86 are electrically coupled to connector rings 24, 26, and 28, respectively via conductors 74, 76, and 78a. Conductors 72, 74, 76 and 78a, extending through body 30 to adaptor connector terminal 20, are electrically isolated from one another.

FIG. 2 further illustrates receptacle port 34 including a high-voltage contact 90 for providing electrical connection to lead connector pin 64 of second lead 60. Contact 90 is electrically coupled to a conductor 78b, which is further coupled to connector ring 28 of connector terminal 20. Thus, according to some embodiments of the present invention, adaptor 16 performs as a signal splitter, providing common electrical connection for two high-voltage contacts 86 and 90 adapted to engage with high-voltage connector elements 50 and 64 located on separate leads 40 and 60, thereby enabling electrode 66 of second lead 60 to augment high-voltage therapy delivery of first lead 40.

Adaptor body 30 and external portions of receptacle 32 and 34 and connector assembly 20 may be formed from a biocompatible, insulating material known for use in manufacturing medical electrical leads. Appropriate materials include, but are not limited to, a polyurethane or silicone rubber. Conductors 72, 74, 76 and 78a may be provided as straight wire conductors, cabled conductors, coiled conductors or other types of conductors known for use in medical electrical leads or adaptors. Conductors 72, 74, 76, and 78a may extend through individual lumens formed within adaptor body 30 or may be individually insulated by a polymeric coating or tubing, such as PTFE or ETFE, and extend through a common central lumen formed within adaptor body 30.

While conductor 78b is shown coupled to contact 90 at a first end and connector ring 28 at a second end, the second end may alternatively be coupled to a node any where along conductor 78a. In this way, the high-voltage contact 84 of receptacle 32 and high-voltage contact 90 of receptacle 34 are both electrically coupled to the high-voltage connector ring 28 of adaptor connector terminal 20. In alternative embodiments, conductor 78b may be coupled to connector ring 26 or anywhere along conductor 76 such that a signal from connector ring 26 is split to high-voltage contact 84 of receptacle 32 via conductor 76 and to high-voltage contact 90 via conductor 78b.

Thus, an additional lead 60 including a high-voltage coil electrode 66 may be coupled to IMD 10 having a single connector port 14. Adaptor 16 allows placement of an additional, high-voltage lead in operative relation to the heart, without requiring a different IMD having an additional connector port, in order to achieve improved cardioversion or defibrillation thresholds when thresholds achieved with a single lead are unacceptably high.

It is recognized that in some embodiments according to the present invention a first lead may have only one high-voltage electrode, for example electrode 54 of lead 40 illustrated in FIG. 1; in this case, when a vector created between electrode 54 and can 11, acting as an electrode, does not provide an acceptably low defibrillation threshold a second lead including a high-voltage electrode, for example electrode 66 of lead 60, is coupled with the first lead to IMD 10 via adaptor 16 such that electrode 54 of the first lead is electrically coupled via contact 84 of first port 32, and electrode 66 of second lead 60 is coupled via contact 90 of second port 34 (FIG. 2). According to these embodiments contact 86 and conductor 78a are not necessary elements of adaptor 16. Additional alternate embodiments employ a switch as illustrated in FIG. 3.

Figure 3:
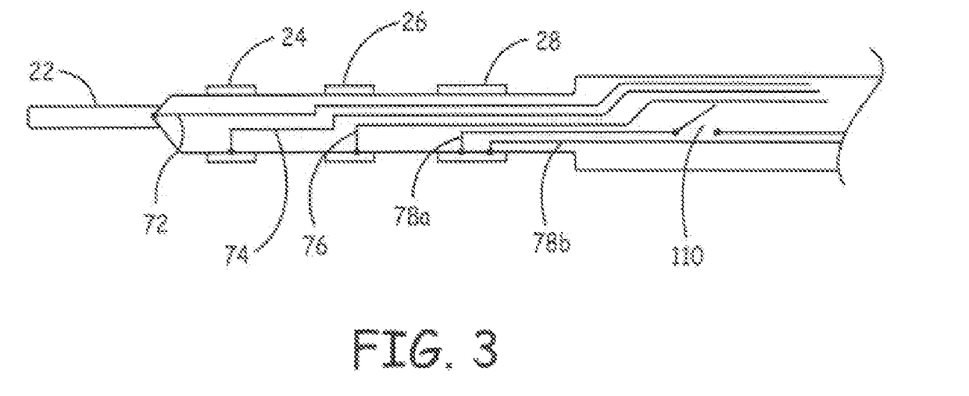
FIG. 3 is a sectional view of the connector terminal portion of an alternative embodiment of the adaptor of FIG. 2.

FIG. 3 is a sectional view of the connector terminal portion of an alternative embodiment of the adaptor of FIG. 2 wherein a switch 110 is provided to allow electrical decoupling of a receptacle contact. When defibrillation thresholds achieved using coil electrodes on a first lead, for example electrodes 54 and 52 of lead 40 shown in FIG. 1, are unacceptably high such that placement of a second high-voltage lead, for example lead 60, is required, it may be desirable to provide a high-voltage signal to the second lead without providing the same high-voltage signal to a coil electrode on the first lead. As such, switch 110 is provided between connector ring 28 and conductor 78a or anywhere along conductor 78a, which is coupled to contact 86 as shown previously in FIG. 2. Switch 110 may be an electrically-, mechanically-, or magnetically-actuated switch. With switch 110 normally closed, a signal delivered to connector ring 28 is split between contact 86 of receptacle 32 and contact 90 of receptacle 34 via conductors 78a and 78b, respectively. When switch 110 is opened, contact 86 is electrically disconnected from connector ring 28 such that a signal delivered to connector ring 28 is conducted only to contact 90 via conductor 78b.

Figure 4:
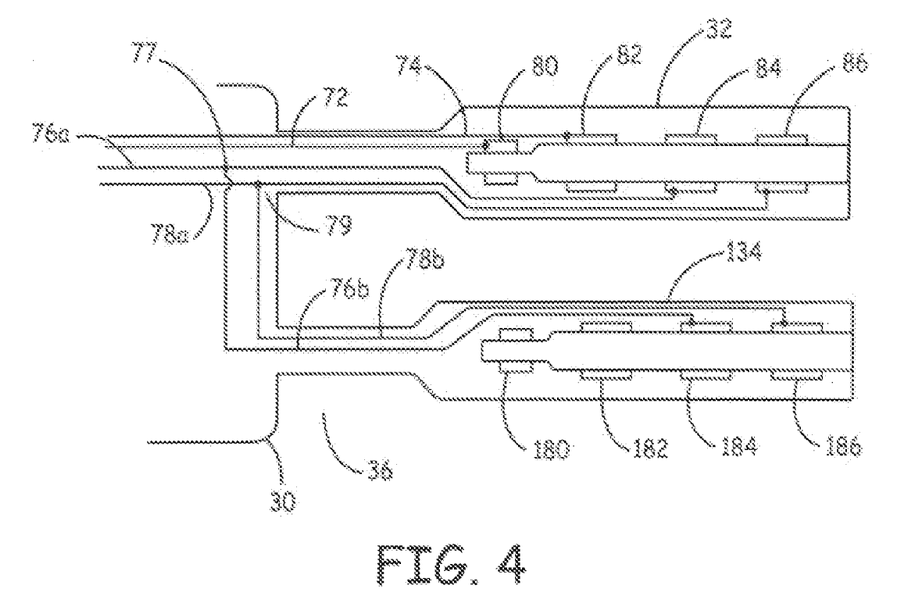
FIG. 4 is a sectional view of an alternative embodiment of the adaptor of FIG. 2.

FIG. 4 is a sectional view of an alternative embodiment of the adaptor of FIG. 2 wherein a second port 134 is adapted to engage another multi-polar lead including a connector terminal similar to that of first lead 40 illustrated in FIG. 1. According to this embodiment, signals delivered to two high-voltage connector rings are split to contacts engaging with connector elements of two separate leads. As such, receptacle 134 includes four contacts 180, 182, 184, and 186. Conductor 78b is shown in FIG. 4 to be coupled at one end to high-voltage contact 186 and at the other end to conductor 78a at node 79, which may be located anywhere along the length of conductor 78a. Conductor 78a is further coupled to connector ring 28 of adaptor connector terminal 20 (FIGS. 2 and 3). Conductor 76b is coupled at one end to high-voltage contact 184 and at the other end to conductor 76a at node 77, which may be located anywhere along the length of conductor 76a. Conductor 76a is further coupled to connector ring 26 on adaptor connector terminal 20 (FIGS. 2 and 3). Thus, both high-voltage connector rings 26 and 28 of adaptor connector terminal 20 are coupled to high-voltage contacts in receptacles 32 and 134 allowing connection of two leads, each having two high-voltage coil electrodes, to a single connection port of an IMD. Signals delivered to connector ring 26 are split between contacts 84 and 184 and signals delivered to connector ring 28 are split between contacts 86 and 186. In alternative embodiments, conductors 76*b* and 78*b* may be coupled directly to connector rings 26 and 28 of connector terminal 20 rather than to nodes 77 and 79 as shown in FIG. 4. Contacts 180 and 182 may be left inactive as shown in FIG. 4, i.e., having no electrical connection to conductors extending to adaptor connector terminal 20. In other embodiments, additional conductors may be provided for coupling additional contacts that may be present in receptacle 134 to connector elements included in connector terminal 20.

Figure 5:
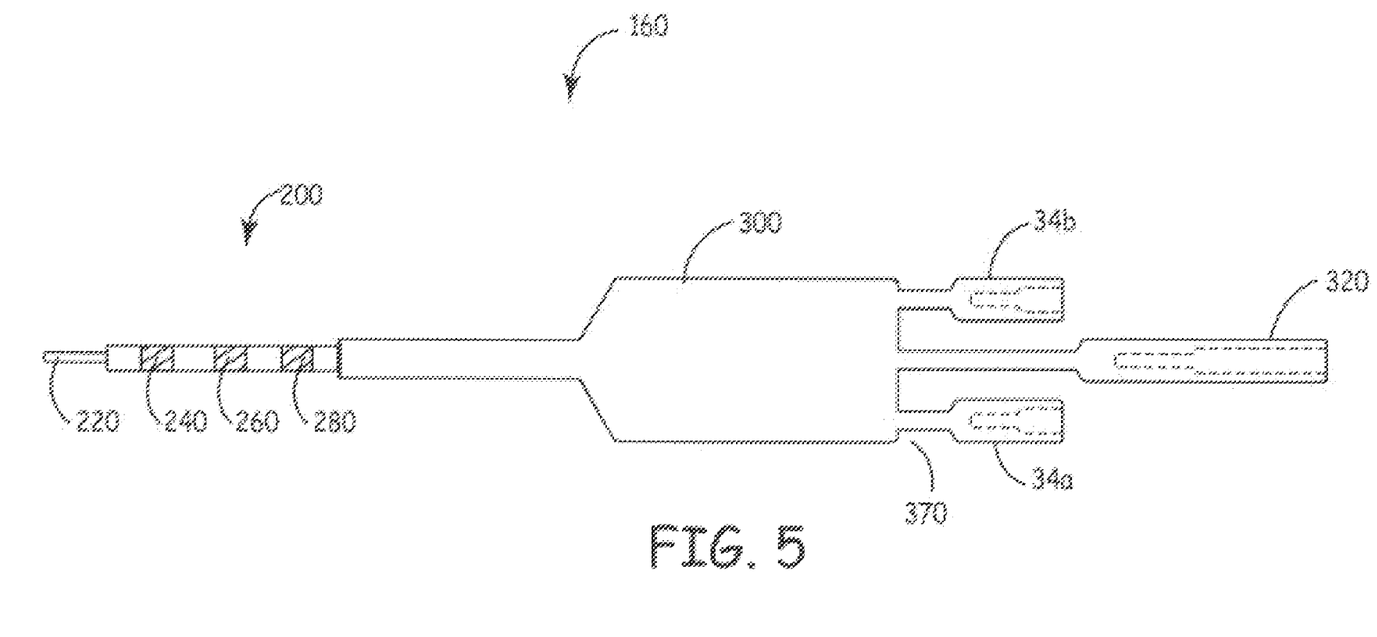
FIG. 5 is a plan view of a trifurcated adaptor according to an alternate embodiment of the present invention.

FIG. 5 is a plan view of yet another embodiment of an adaptor 160 provided for splitting signals delivered to two high-voltage contacts engaging connector elements located on a first lead, for example connector elements 48 and 50 of lead 40 illustrated in FIG. 1, and two additional high-voltage contacts located in two separate ports 34*a* and 34*b* for engaging connector elements of two separate leads, for example 64 of lead 60. FIG. 5 illustrates a connector terminal 20 of adaptor 160 extending from an adaptor body 300 and including a connector pin 220 and connector rings 240, 260 and 280. Three receptacle ports 32, 34*a* and 34*b* extend from a trifurcation 370 at the opposite end of adaptor body 300.

Figure 6:
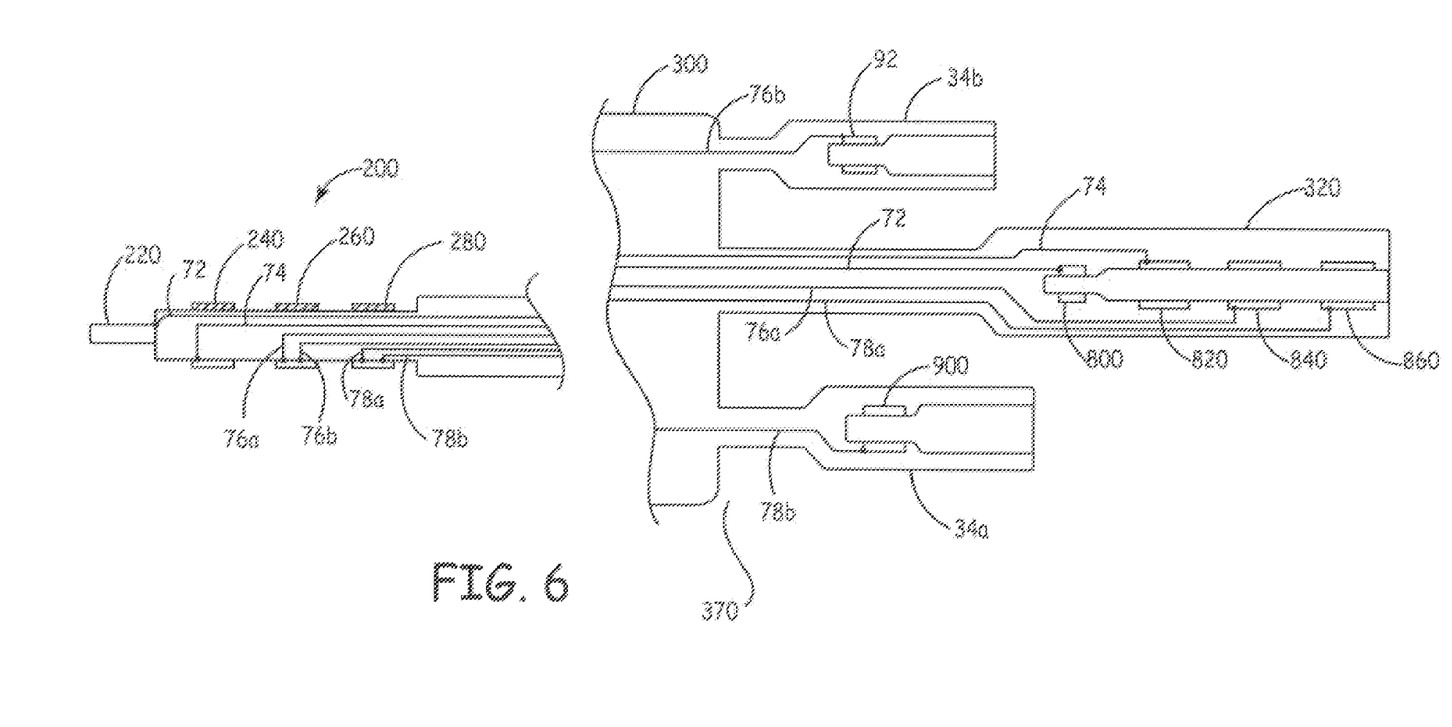
FIG. 6 is a sectional view of the adaptor of FIG. 5.

As shown in more detail in the sectional view of FIG. 6, receptacle port 320 includes include low-voltage contacts 800 and 820 and high-voltage contacts 840 and 860 for providing electrical connection to lead connector elements 44, 46, 48, and 50 respectively (FIG. 1); contact 800 is coupled to connector pin 220 and via a conductor 72 and each of contacts 820, 840, and 860 are electrically coupled to connector rings 240, 260, and 280, respectively via conductors 74, 76*a*, and 78*a*. Conductors 72, 74, 76*a* and 78*a*, extending through body 30 to adaptor connector terminal 20, are electrically isolated from one another.

FIG. 6 further illustrates receptacle ports 34*a* and 34*b* each including a single, high-voltage contact 900 and 92, respectively. Ports 34*a* and 34*b* may be adapted to receive standard DF-1 lead connectors. Conductor 78*b* is coupled between contact 900 of receptacle port 34*a* and connector ring 280 of adaptor connector terminal 200 such that signals delivered to connector ring 280 are split between contact 860 of receptacle port 320 and contact 900 via conductors 78*a* and 78*b*, respectively. Conductor 76*b* is coupled between contact 920 of receptacle port 34*b* and connector ring 260 of adaptor connector terminal 200. Signals delivered to connector ring 260 are split between contact 840 of receptacle port 320 and contact 92 via conductors 76*a* and 76*b*, respectively. Adaptor 160 of FIGS. 5 and 6 thus allows connection of two additional high-voltage leads to an IMD having a single connection port, for example IMD 10 shown in FIG. 1.

Illustrative embodiments of systems incorporating a medical lead adaptor allowing one or more additional high-voltage leads to be connected to an IMD having a single connection port have been described herein. While the present invention has been described in the context of specific embodiments, these embodiments are intended to be exemplary and are not intended to limit the scope, applicability, or configuration of the invention in any way. It should be understood that various changes may be made in the function and arrangement of elements described in exemplary embodiments without departing from the scope of the invention as set forth in the appended claims.

What is claimed is:

1. A medical system, comprising:
a first lead including a first electrode adapted for high-voltage therapy, a second electrode, a first elongated insulated conductor, a second elongated insulated conductor and a lead connector terminal; the lead connector terminal including a first connector element coupled to the first electrode via the first elongated conductor and a second connector element coupled to the second electrode via the second elongated conductor;

a second lead including an electrode adapted for high-voltage therapy, an elongated insulated conductor, and a lead connector terminal; the lead connector terminal including a connector element coupled to the electrode via the elongated conductor;

an adaptor including a connector terminal, a first port engaging the first lead connector terminal, and a second port engaging the second lead connector terminal; and an IMD including a connector port adapted to engage the adaptor connector terminal, the connector port including a first high-voltage connector and a second high-voltage connector;

wherein, the first port of the adaptor includes a first contact coupled to the first connector element of the first lead connector terminal and a second contact isolated from the first contact and coupled to the second connector element of the first lead connector terminal engaged within the first port;

the second port of the adaptor includes a contact coupled to the connector element of the second lead connector terminal engaged within the second port; and the connector terminal of the adaptor includes a first connector ring adapted for electrical coupling with the first high-voltage connector of the IMD port and coupled to the first contact of the first adaptor port via a first insulated conductor, and a second connector ring adapted for electrical coupling with the second high-voltage connector of the IMD port and coupled to the contact of the second adaptor port via a second insulated conductor.

2. The medical system of claim 1, wherein:
the second electrode of the first lead is adapted for low-voltage therapy;
the connector port of the IMD further includes a low-voltage connector; and
the adaptor connector terminal further includes a third connector ring adapted for electrical coupling with the low-voltage connector of the IMD port and coupled to the second contact of the first adaptor port via a third insulated conductor.

3. The medical system of claim 1, wherein:
the second electrode of the first lead is adapted for high-voltage therapy; and
the second connector ring of the adaptor connector terminal is further coupled to the second contact of the first adaptor port via a third insulated conductor.

4. The medical system of claim 1, wherein the adaptor further includes a switch adapted to reversibly open the third conductor thereby reversibly decoupling the second contact of the first adaptor port from the second connector ring of the adaptor connector terminal.

5. The medical system of claim 3, wherein
the first lead further includes a third electrode adapted for low-voltage therapy and a third elongated insulated conductor;
the first lead connector terminal further includes a third connector element coupled to the third electrode via the third elongated conductor;
the connector port of the IMD further includes a low-voltage connector; and
the adaptor connector terminal further includes a third connector ring adapted for electrical coupling to the low-voltage connector of the IMD port and coupled to the third connector element via a fourth insulated conductor.

6. The medical system of claim 1, further comprising;
a third lead including an electrode adapted for high-voltage therapy, an elongated insulated conductor, and a lead connector terminal; the lead connector terminal of the third lead including a connector element coupled to the electrode of the third lead via the elongated conductor of the third lead; and wherein
the adaptor further includes a third port engaging the connector terminal of the third lead;
the third port includes a contact coupled to the connector element of the third lead connector terminal engaged within the third port; and
the first connector ring of the connector terminal of the adaptor is coupled to the contact of the third port via a third insulated conductor.

7. The medical system of claim 1, further comprising;
a third lead including an electrode adapted for high-voltage therapy, an elongated insulated conductor, and a lead connector terminal; the lead connector terminal of the third lead including a connector element coupled to the electrode of the third lead via the elongated conductor of the third lead; and wherein
the adaptor further includes an third port engaging the connector terminal of the third lead;
the third port includes a contact coupled to the connector element of the third lead connector terminal engaged within the third port; and
the second connector ring of the connector terminal of the adaptor is coupled to the contact of the third port via a third insulated conductor.

8. A medical system, comprising:
a first lead including a first electrode adapted for high-voltage therapy, a second electrode adapted for high-voltage therapy, a first elongated insulated conductor, a second elongated insulated conductor and a lead connector terminal; the lead connector terminal including a first connector element coupled to the first electrode via the first elongated conductor and a second connector element coupled to the second electrode via the second elongated conductor;
a second lead including an electrode adapted for high-voltage therapy, an elongated insulated conductor, and a lead connector terminal; the lead connector terminal including a connector element coupled to the electrode via the elongated conductor;
an IMD including a connector port, the connector port including a first high-voltage connector and a second high-voltage connector; and
means for converting the first lead connector terminal and the second lead connector terminal into a single connector terminal for engagement within the IMD port;
wherein engagement of the single connector terminal in the IMD port results in coupling the first connector element of the first lead connector terminal and the connector element of the second lead connector terminal to the first high-voltage connector and coupling the second connector element of the first lead connector terminal to the second high-voltage connector.

9. A medical system, comprising:
a first lead including a first electrode adapted for high-voltage therapy, a second electrode adapted for high-voltage therapy, a first elongated insulated conductor, a second elongated insulated conductor and a lead connector terminal; the lead connector terminal including a first connector element coupled to the first electrode via the first elongated conductor and a second connector element coupled to the second electrode via the second elongated conductor;
a second lead including an electrode adapted for high-voltage therapy, an elongated insulated conductor, and a lead connector terminal; the lead connector terminal including a connector element coupled to the electrode via the elongated conductor;
an IMD including a connector port, the connector port including a first high-voltage connector, a second high-voltage connector, and a low-voltage connector; and
means for converting the first lead connector terminal and the second lead connector terminal into a single connector terminal for engagement within the IMD port;
wherein engagement of the single connector terminal in the IMD port results in coupling the first connector element of the first lead connector terminal to the first high-voltage connector, coupling the second connector element of the first lead connector to the second high-voltage connector, and coupling the connector element of the second lead connector terminal to the second high-voltage connector;
wherein the means for converting comprises means for reversibly decoupling the second electrode of the first lead from the second high-voltage connector.

10. A medical system, comprising:
a first lead including a first electrode adapted for high-voltage therapy, a second electrode adapted for high-voltage therapy, a first elongated insulated conductor, a second elongated insulated conductor and a lead connector terminal; the lead connector terminal including a first connector element coupled to the first electrode via the first elongated conductor and a second connector element coupled to the second electrode via the second elongated conductor;
a second lead including an electrode adapted for high-voltage therapy, an elongated insulated conductor, and a lead connector terminal; the lead connector terminal including a connector element coupled to the electrode via the elongated conductor;
an adaptor including an in-line connector terminal, a first port engaging the first lead connector terminal, and a second port engaging the second lead connector terminal; and
an IMD including a connector port adapted to engage the adaptor connector terminal, the connector port including a first high-voltage connector and a second high-voltage connector;
wherein, the first port of the adaptor includes a first contact coupled to the first connector element of the first lead connector terminal and a second contact isolated from the first contact and coupled to the second connector element of the first lead connector terminal engaged within the first port;
the second port of the adaptor includes a contact coupled to the connector element of the second lead connector terminal engaged within the second port; and
the connector terminal of the adaptor includes a first connector ring adapted for electrical coupling with the first high-voltage connector of the IMD port and coupled to the first contact of the first adaptor port via a first insulated conductor, and a second connector ring adapted for electrical coupling with the second high-voltage connector of the IMD port and coupled to the contact of the second adaptor port via a second insulated conductor, the second connector ring being further coupled to the second contact of the first adaptor port via a third insulated conductor;
wherein the adaptor further includes a switch positioned along the third conductor and adapted to reversibly open the third conductor thereby reversibly decoupling the second contact of the first adaptor port from the second connector ring of the adaptor connector terminal.

* * * * *